(12) United States Patent
Barnes

(10) Patent No.: US 10,124,484 B1
(45) Date of Patent: Nov. 13, 2018

(54) LOAD-BEARING POWERED EXOSKELETON USING ELECTROMYOGRAPHIC CONTROL

(71) Applicant: Lockheed Martin Corporation, Bethesda, MD (US)

(72) Inventor: Gavin A. Barnes, Saint Cloud, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 156 days.

(21) Appl. No.: 15/371,709

(22) Filed: Dec. 7, 2016

Related U.S. Application Data

(60) Provisional application No. 62/264,547, filed on Dec. 8, 2015.

(51) Int. Cl.
    *B25J 9/00* (2006.01)
    *A61B 5/0492* (2006.01)
    *B25J 9/16* (2006.01)

(52) U.S. Cl.
    CPC ........... *B25J 9/0006* (2013.01); *A61B 5/0492* (2013.01); *B25J 9/1694* (2013.01); *Y10S 901/46* (2013.01)

(58) Field of Classification Search
    CPC ..... B25J 9/0006; B25J 9/1694; A61B 5/0492; Y10S 901/46
    USPC .................................................. 700/245, 258
    See application file for complete search history.

(56) References Cited

U.S. PATENT DOCUMENTS

| | | |
|---|---|---|
| 2,010,482 A | 8/1935 | Cobb |
| 3,964,182 A | 6/1976 | Pomeret et al. |
| 4,258,556 A | 3/1981 | Ruyten et al. |
| 5,016,869 A | 5/1991 | Dick et al. |

(Continued)

FOREIGN PATENT DOCUMENTS

| | | |
|---|---|---|
| JP | H03105191 U | 10/1991 |
| JP | 3024978 U | 6/1996 |

(Continued)

OTHER PUBLICATIONS

Notice of Allowance and Notice Requiring Inventor's Oath or Declaration for U.S. Appl. No. 14/744,892, dated Jul. 5, 2017, 11 pages.

(Continued)

*Primary Examiner* — Jaime Figueroa
(74) *Attorney, Agent, or Firm* — Withrow & Terranova, PLLC

(57) ABSTRACT

An exoskeleton joint for a load-bearing powered exoskeleton includes a first exoskeleton link supporting a weight of an external load being applied to the powered exoskeleton and a second exoskeleton link that transfers the weight of the external load to a support surface, i.e., to the ground. In response to a contraction of a muscle of a human user associated with the exoskeleton joint, an electromyography (EMG) sensor generates EMG sensor data based on the muscle contraction. A controller receives the EMG sensor data, determines an actuator command based on the EMG sensor data, and communicates the actuator command to an actuator associated with the exoskeleton joint. This has the advantage that the exoskeleton joint associated with the human user's joint can be instructed to move in response to contraction of the muscle of the human user before the muscle causes the human user's joint to actually move.

18 Claims, 6 Drawing Sheets

(56) References Cited

U.S. PATENT DOCUMENTS

| | | | |
|---|---|---|---|
| 5,020,790 A * | 6/1991 | Beard | A61F 5/0102 482/4 |
| 5,865,426 A | 2/1999 | Kazerooni | |
| 5,993,404 A | 11/1999 | McNiel | |
| 6,886,812 B2 | 5/2005 | Kazerooni | |
| 6,913,583 B2 | 7/2005 | Jestrabek-Hart | |
| 7,153,242 B2 | 12/2006 | Goffer | |
| 7,163,518 B1 | 1/2007 | Roche et al. | |
| 7,571,839 B2 | 8/2009 | Chu et al. | |
| 7,628,766 B1 | 12/2009 | Kazerooni et al. | |
| 7,883,546 B2 | 2/2011 | Kazerooni et al. | |
| 7,947,004 B2 | 5/2011 | Kazerooni et al. | |
| 8,057,410 B2 | 11/2011 | Angold et al. | |
| 8,070,700 B2 | 12/2011 | Kazerooni et al. | |
| 8,171,570 B2 | 5/2012 | Adarraga | |
| 8,231,688 B2 | 7/2012 | Fairbanks et al. | |
| 8,257,291 B2 | 9/2012 | Kazerooni et al. | |
| 8,394,038 B2 | 3/2013 | Ashihara et al. | |
| 8,672,865 B2 | 3/2014 | Franke et al. | |
| 8,702,632 B2 | 4/2014 | Han et al. | |
| 8,801,641 B2 | 8/2014 | Kazerooni et al. | |
| 8,894,592 B2 | 11/2014 | Amundson et al. | |
| 8,945,028 B2 | 2/2015 | Kazerooni et al. | |
| 8,968,222 B2 | 3/2015 | Kazerooni et al. | |
| 9,011,354 B2 | 4/2015 | Angold et al. | |
| 9,333,644 B2 | 5/2016 | Angold | |
| 9,492,300 B2 | 11/2016 | Bujold et al. | |
| 9,662,262 B2 | 5/2017 | Hollander et al. | |
| 2003/0073552 A1 | 4/2003 | Knight | |
| 2003/0109817 A1 | 6/2003 | Berl | |
| 2003/0115954 A1 | 6/2003 | Zemlyakov et al. | |
| 2005/0137717 A1 | 6/2005 | Gramnas et al. | |
| 2006/0064047 A1 | 3/2006 | Shimada et al. | |
| 2006/0107433 A1 | 5/2006 | Olson | |
| 2006/0260620 A1 | 11/2006 | Kazerooni et al. | |
| 2007/0056592 A1 | 3/2007 | Angold et al. | |
| 2007/0123997 A1 | 5/2007 | Herr et al. | |
| 2007/0233279 A1 | 10/2007 | Kazerooni et al. | |
| 2008/0234608 A1 | 9/2008 | Sankai | |
| 2009/0210093 A1 | 8/2009 | Jacobsen et al. | |
| 2009/0292369 A1 * | 11/2009 | Kazerooni | A61H 3/00 623/27 |
| 2010/0076360 A1 | 3/2010 | Shimada et al. | |
| 2010/0094185 A1 | 4/2010 | Amundson et al. | |
| 2010/0152630 A1 | 6/2010 | Matsuoka et al. | |
| 2010/0324699 A1 * | 12/2010 | Herr | A61F 2/66 623/27 |
| 2011/0040216 A1 | 2/2011 | Herr et al. | |
| 2011/0105966 A1 | 5/2011 | Kazerooni et al. | |
| 2011/0166489 A1 | 7/2011 | Angold et al. | |
| 2011/0201978 A1 | 8/2011 | Jeon et al. | |
| 2011/0214524 A1 | 9/2011 | Jacobsen et al. | |
| 2011/0264014 A1 | 10/2011 | Angold | |
| 2011/0266323 A1 | 11/2011 | Kazerooni et al. | |
| 2012/0004736 A1 * | 1/2012 | Goldfarb | A61F 2/60 623/25 |
| 2012/0172770 A1 * | 7/2012 | Almesfer | B25J 9/0006 601/35 |
| 2012/0283845 A1 | 11/2012 | Herr et al. | |
| 2012/0292361 A1 | 11/2012 | Thiruppathi | |
| 2013/0023800 A1 | 1/2013 | Bédard et al. | |
| 2013/0102935 A1 | 4/2013 | Kazerooni et al. | |
| 2013/0150980 A1 | 6/2013 | Swift et al. | |
| 2013/0197408 A1 | 8/2013 | Goldfarb et al. | |
| 2013/0231595 A1 | 9/2013 | Zoss et al. | |
| 2013/0237884 A1 * | 9/2013 | Kazerooni | H05K 999/99 601/34 |
| 2013/0296746 A1 | 11/2013 | Herr et al. | |
| 2013/0303950 A1 * | 11/2013 | Angold | B25J 9/0006 601/35 |
| 2013/0331744 A1 | 12/2013 | Kamon | |
| 2014/0046234 A1 | 2/2014 | DeSousa | |
| 2014/0200491 A1 | 7/2014 | Julin et al. | |
| 2014/0276264 A1 | 9/2014 | Caires et al. | |
| 2014/0330431 A1 | 11/2014 | Hollander et al. | |
| 2014/0358053 A1 | 12/2014 | Triolo et al. | |
| 2015/0001269 A1 * | 1/2015 | Sacksteder | B25J 9/0006 224/576 |
| 2015/0081036 A1 | 3/2015 | Nakanishi et al. | |
| 2015/0134080 A1 * | 5/2015 | Roh | B25J 9/0006 623/32 |
| 2015/0173992 A1 | 6/2015 | Wang | |
| 2015/0313786 A1 | 11/2015 | Sano | |
| 2015/0321340 A1 * | 11/2015 | Smith | B25J 9/10 74/490.01 |
| 2015/0366694 A1 | 12/2015 | Bujold et al. | |
| 2016/0015589 A1 | 1/2016 | Lee et al. | |
| 2016/0016307 A1 | 1/2016 | Choi et al. | |
| 2016/0038313 A1 | 2/2016 | Kim et al. | |
| 2016/0058647 A1 * | 3/2016 | Maddry | B25J 9/0006 623/26 |
| 2016/0184165 A1 | 6/2016 | Ohta et al. | |
| 2016/0262969 A1 | 9/2016 | Ohta et al. | |
| 2017/0061828 A1 * | 3/2017 | Artemiadis | G09B 23/30 |
| 2017/0181917 A1 | 6/2017 | Ohta et al. | |
| 2017/0303849 A1 * | 10/2017 | De Sapio | A61B 5/1117 |

FOREIGN PATENT DOCUMENTS

| | | |
|---|---|---|
| JP | 2003104682 A | 4/2003 |
| JP | 200911818 A | 1/2009 |
| WO | 2012154580 A1 | 11/2012 |
| WO | 2014159608 A1 | 10/2014 |

OTHER PUBLICATIONS

Corrected Notice of Allowance for U.S. Appl. No. 14/744,892, dated Jul. 14, 2017, 7 pages.

Whitwam, Ryan, et al., "Banks now have money-grabbing robotic exoskeletons that are probably helpful for robbing banks," PCMag Digital Group, May 9, 2015, Ziff Davis, LLC, www.geek.com/?s=japanese+banks+now+have+money+grabbing&x=0&y=0, 4 pages.

Non-Final Office Action for U.S. Appl. No. 131084,265, dated Sep. 10, 2015, 7 pages.

Extended European Search Report for European Patent Application No. 11766862.4, dated May 27, 2014, 4 pages.

Notice of Reasons for Refusal for Japanese Patent Application No. 2013-504019, dated Feb. 24, 2015, 6 pages.

International Search Report for PCT/US2011/031956, dated Jun. 21, 2011, 2 pages.

International Preliminary Report on Patentability for PCT/US2011/031956, dated Oct. 9, 2012, 6 pages.

Supplemental Notice of Allowability for U.S. Appl. No. 13/084,265, dated Jan. 25, 2016, 3 pages.

Notice of Reasons for Refusal for Japanese Patent Application No. 2013-504019, dated Dec. 22, 2015, 6 pages.

Decision to Grant for Japanese Patent Application No. 2013-504019, dated Aug. 16, 2016, 6 pages.

International Search Report and Written Opinion for International Patent Application No. PCT/US2016/042427, dated Oct. 24, 2016, 18 pages.

Artemiadis, Panagiotis K. et al., "EMG-based Position and Force Estimates in Coupled Human-Robot Systems: Towards EMG-controlled Exoskeletons," Experimental Robotics: The Eleventh International Symposium (book), vol. 54, 2009, Springer Berlin Heidelberg, pp. 1-10.

Ferris, Daniel P. et al., "An Ankle-Foot Orthosis Powered by Artificial Muscles," Journal of Applied Biomechanics, vol. 21, Issue 2, May 2005, Human Kinetics, Inc., 3 pages.

Ferris, Dan et al., "An Improved Ankle-Foot Orthosis Powered by Artificial Pneumatic Muscles," XIXth Congress of the International Society of Biomechanics: the human body in motion, Jul. 6-11, 2003, Dunedin, New Zealand, University of Otago, 17 pages.

Ferris, Daniel P. et al., "Development of a myoelectrically controlled lower limb orthosis for human locomotion," Proceedings of the NCMRR Symposium "Medical Rehab on the Move: Spotlight

(56) References Cited

OTHER PUBLICATIONS on BioEngineering," Abstract, Jan. 4-5, 2001, Bethesda, Maryland, Supported by NIH AR08602 and U.S. Dept. of Veterans Affairs Center Grant #A0806C, 2 pages.

Gordon, Keith E. et al., "Motor Adaptation During Walking with a Powered Ankle Foot Orthosis," Journal of NeuroEngineering and Rehabilitation, vol. 4, 2007, BioMed Central Ltd, 2 pages.

Kawamoto, Hiroaki et al., "Power Assist Method for HAL-3 using EMG-based Feedback Controller," IEEE International Conference on Systems, Man and Cybernetics, Oct. 8, 2003, IEEE, pp. 1648-1653.

Sawicki, Gregory S. et al., "A Knee-Ankle-Foot Orthosis (KAFO) Powered by Artificial Pneumatic Muscles," XIXth Congress of the International Society of Biomechanics: the human body in motion, Jul. 6-11, 2003, Dunedin, New Zealand, 1 page.

Sawicki, Gregory S. et al., "Mechanics and energetics of level walking with powered ankle exoskeletons," The Journal of Experimental Biology, vol. 211, Feb. 19, 2009, The Company of Biologists, pp. 1402-1413.

Non-Final Office Action and Examiner-Initiated Interview Summary for U.S. Appl. No. 14/744,892, dated Feb. 17, 2017, 44 pages.

Non-Final Office Action for U.S. Appl. No. 15/181,934, dated Mar. 27, 2018, 17 pages.

International Preliminary Report on Patentability for PCT/US2016/042427, dated Jan. 23, 2018, 13 pages.

Non-Final Office Action for U.S. Appl. No. 14/801,941, dated Apr. 25, 2018, 9 pages.

U.S. Appl. No. 13/084,265, filed Apr. 11, 2011, now U.S. Pat. No. 9,333,644.

U.S. Appl. No. 14/801,941, filed Jul. 17, 2015.

U.S. Appl. No. 14/744,855, filed Jun. 19, 2015.

U.S. Appl. No. 15/181,934, filed Jun. 14, 2016.

U.S. Appl. No. 14/744,892, filed Jun. 19, 2015.

U.S. Appl. No. 15/359,806, filed Nov. 23, 2016.

\* cited by examiner

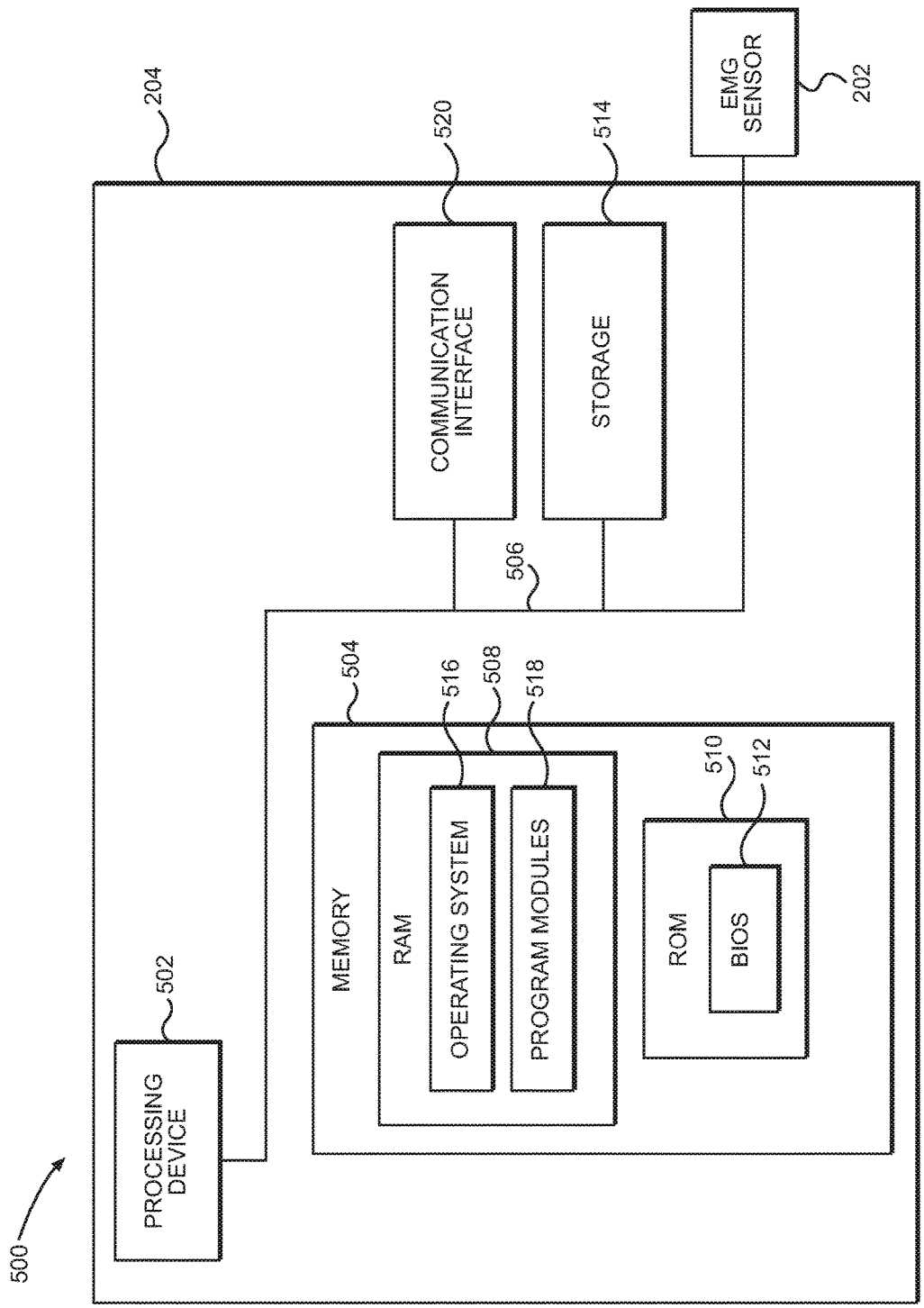

LOAD-BEARING POWERED EXOSKELETON USING ELECTROMYOGRAPHIC CONTROL

RELATED APPLICATION

This application claims the benefit of and priority to U.S. Provisional Application No. 62/264,547, filed on Dec. 8, 2015, entitled "LOAD-BEARING EXOSKELETON CONTROL USING ELECTROMYOGRAPHY FOR DIRECT FORCE AMPLIFICATION," the disclosure of which is hereby incorporated herein by reference in its entirety.

TECHNICAL FIELD

The embodiments relate generally to powered exoskeletons and, in particular, to a load-bearing powered exoskeleton using electromyographic control.

BACKGROUND

Exoskeletons are passive or powered structures worn and controlled by an individual. Exoskeletons allow an individual to manipulate items with less physical exertion than would be possible without the exoskeleton. For example, an exoskeleton may be used to allow a user to move relatively heavy items from one location to another location, or to carry an item over a distance.

A powered exoskeleton applies forces to one or more links of an exoskeleton structure to reduce the amount of force that an individual would otherwise have to apply. However, some conventional exoskeletons rely on mechanical sensors that detect a force being applied by the individual to determine when and how much force to apply to a link. Since these mechanical sensors still require the individual to exert a force against the link before the exoskeleton applies its own force to the link, these arrangements can lead to fatigue. Some conventional powered exoskeletons also rely on algorithms, such as predictive algorithms, to determine when and how much force to apply to a link, but these predictive algorithms do not sufficiently mimic the way individuals naturally move, resulting in the individual at times counteracting against the movement of the exoskeleton, which can also lead to fatigue.

SUMMARY

The embodiments relate generally to powered exoskeletons and, in particular, to a load-bearing powered exoskeleton using electromyographic control. In one embodiment, an exoskeleton joint includes a first exoskeleton link supporting a weight of an external load being applied to the powered exoskeleton and a second exoskeleton link that transfers the weight of the external load to a support surface, i.e., to the ground. In response to a contraction of a muscle of a human user associated with the exoskeleton joint, an electromyography (EMG) sensor generates EMG sensor data based on the muscle contraction. A controller receives the EMG sensor data, determines an actuator command based on the EMG sensor data, and communicates the actuator command to an actuator associated with the exoskeleton joint.

One advantage of this arrangement is that the exoskeleton joint of the load-bearing powered exoskeleton associated with the human user's joint can be instructed to move in response to the muscle contraction of the human user before the muscle causes the human user's joint to actually move. Since the delay between the electrochemical reaction, which causes the muscle contraction, and the actual movement of the human user's joint is greater than the time required for the EMG sensor and the controller to generate and utilize the EMG sensor data to cause the actuator to move, the powered exoskeleton can accurately mimic the actual movements of the human user without the need for conventional reactive or predictive systems, which can lead to fatigue.

In one embodiment, a powered exoskeleton is disclosed. The powered exoskeleton includes a first exoskeleton link configured to support an external load applied to the powered exoskeleton. The powered exoskeleton further includes a second exoskeleton link movably coupled to the first exoskeleton link at an exoskeleton joint, the second exoskeleton link configured to transfer a weight of the external load through the exoskeleton joint to a support surface. The powered exoskeleton further includes an actuator configured to selectively move the first exoskeleton link with respect to the second exoskeleton link. The powered exoskeleton further includes an EMG sensor configured to generate EMG sensor data based on a muscle contraction of a muscle of a human user. The powered exoskeleton further includes a controller communicatively coupled to the EMG sensor and the actuator. The controller is configured to receive the EMG sensor data from the EMG sensor. The controller is further configured to determine an actuator command based on the EMG sensor data to impart an actuator force on at least one of the first exoskeleton link and the second exoskeleton link. The controller is further configured to communicate the actuator command to the actuator to cause the actuator to impart the actuator force on the at least one of the first exoskeleton link and the second exoskeleton link to cause the first exoskeleton link and the second exoskeleton link to move with respect to each other.

According to another embodiment, a method of moving an external load using a powered exoskeleton worn by a human user is disclosed. The method includes supporting an external load applied to the powered exoskeleton through an exoskeleton joint of the powered exoskeleton. The exoskeleton joint includes a first exoskeleton link movably coupled to a second exoskeleton link, the exoskeleton joint configured to transfer a weight of the external load to a support surface. The method further comprises generating EMG sensor data by an EMG sensor based on a muscle contraction of a muscle of the human user. The method further includes determining an actuator command based on the EMG sensor data to impart an actuator force on the first exoskeleton link. The method further includes communicating the actuator command to an actuator coupled to the first exoskeleton link to cause the actuator to impart the actuator force on the first exoskeleton link to move the first exoskeleton link with respect to the second exoskeleton link.

Those skilled in the art will appreciate the scope of the disclosure and realize additional aspects thereof after reading the following detailed description of the embodiments in association with the accompanying drawing figures.

BRIEF DESCRIPTION OF THE DRAWINGS

The accompanying drawing figures incorporated in and forming a part of this specification illustrate several aspects of the disclosure and, together with the description, serve to explain the principles of the disclosure.

FIG. 5 is a block diagram of a computing device suitable for use with components of the powered exoskeleton, such as the system of FIG. 2, for example.

DETAILED DESCRIPTION

Figure 1A:
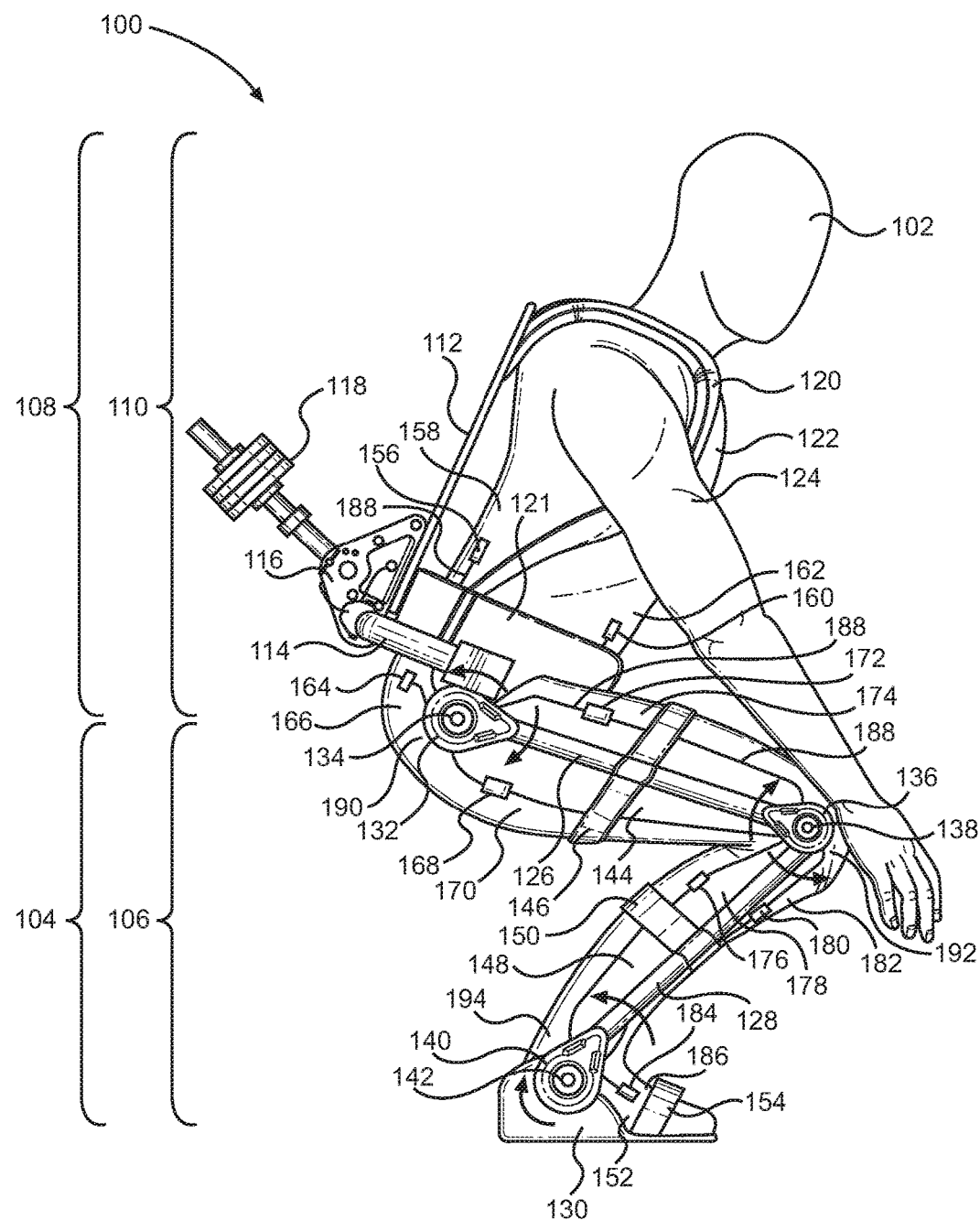
FIGS. 1A and 1B are side views of a powered exoskeleton using electromyography (EMG) for direct force amplification based on movement of a human user, according to an embodiment.

The embodiments set forth below represent the information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Any flowcharts discussed herein are necessarily discussed in some sequence for purposes of illustration, but unless otherwise explicitly indicated, the embodiments are not limited to any particular sequence of steps. The use herein of ordinals in conjunction with an element is solely for distinguishing what might otherwise be similar or identical labels, such as "first exoskeleton link" and "second exoskeleton link," and does not imply a priority, a type, an importance, or other attribute, unless otherwise stated herein. The term "about" used herein in conjunction with a numeric value means any value that is within a range of ten percent greater than or ten percent less than the numeric value.

As used herein and in the claims, the articles "a" and "an" in reference to an element refers to "one or more" of the element unless otherwise explicitly specified.

The embodiments relate generally to powered exoskeletons and, in particular, to a load-bearing powered exoskeleton using electromyographic control. In one embodiment, an exoskeleton joint includes a first exoskeleton link supporting a weight of an external load being applied to the powered exoskeleton and a second exoskeleton link that transfers the weight of the external load to a support surface, i.e., to the ground. In response to a contraction of a muscle of a human user associated with the exoskeleton joint, an electromyography (EMG) sensor generates EMG sensor data based on the muscle contraction. A controller receives the EMG sensor data, determines an actuator command based on the EMG sensor data, and communicates the actuator command to an actuator associated with the exoskeleton joint.

One advantage of this arrangement is that the exoskeleton joint of the load-bearing powered exoskeleton associated with the human user's joint can be instructed to move in response to the muscle contraction of the human user before the muscle causes the human user's joint to actually move. Since the delay between the electrochemical reaction, which causes the muscle contraction, and the actual movement of the human user's joint is greater than the time required for the EMG sensor and the controller to generate and utilize the EMG sensor data to cause the actuator to move, the powered exoskeleton can accurately mimic the actual movements of the human user without the need for conventional reactive or predictive systems, which can lead to fatigue.

As used herein, the term "electromyography" or "EMG" refers to the detection and recording of the electrical activity of muscle tissue resulting from electrochemical reactions in the muscle tissue. When EMG is used with skeletal muscle tissue, i.e., muscles operatively connected to one or more skeletal bones (or other types of body segments), EMG can detect contraction of the muscle tissue before the muscle tissue has contracted with sufficient force to actually move the joint.

Figure 1B:
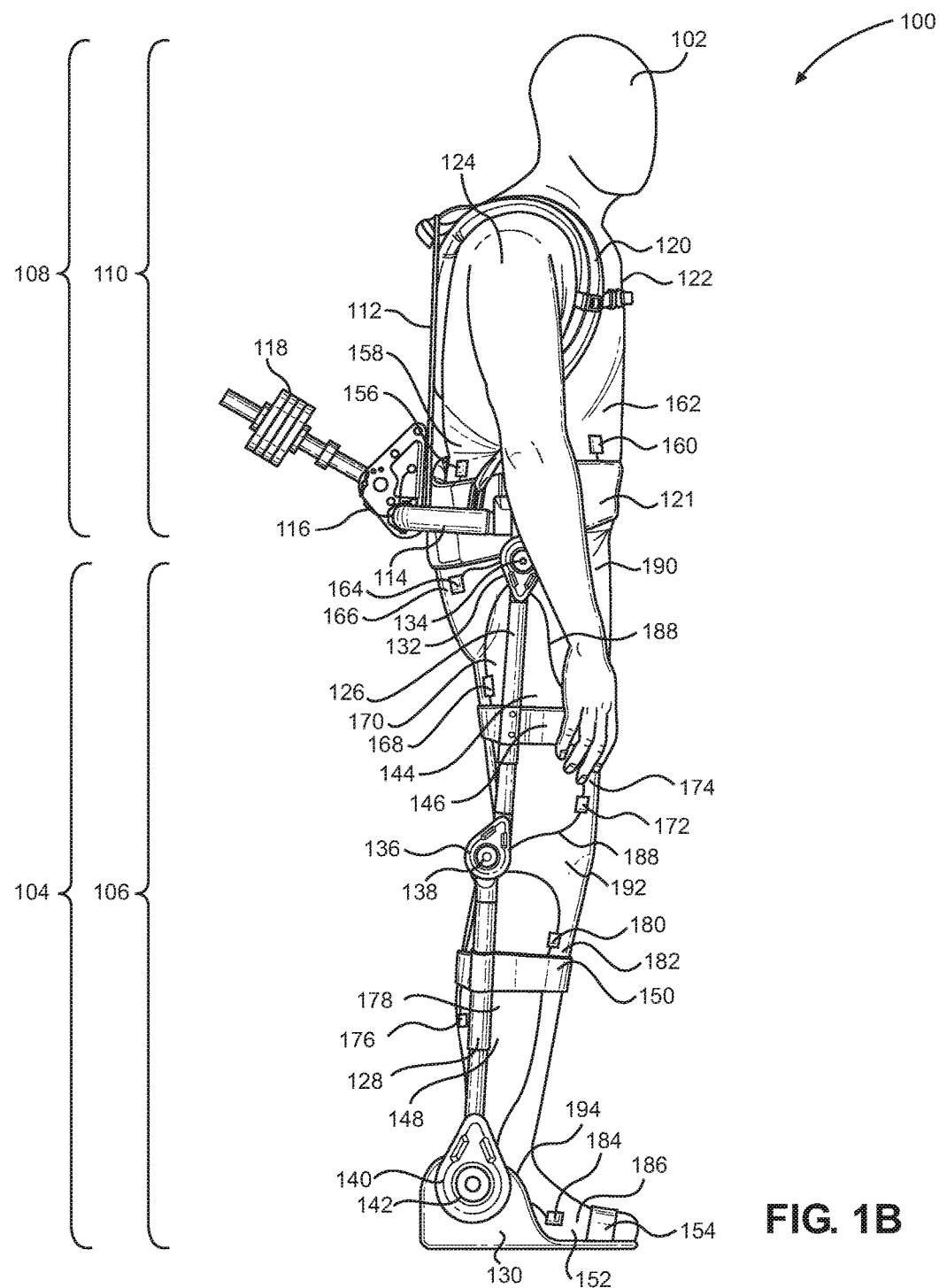

In this regard, FIGS. 1A and 1B are side views of a powered exoskeleton 100 using EMG for direct force amplification based on movement of a human user 102, accordingly to an embodiment. The powered exoskeleton 100 in this example is a full body exoskeleton having a lower body exoskeleton 104 configured to be worn by a lower body 106 of the human user 102 and an upper body exoskeleton 108 configured to be worn by an upper body 110 of the human user 102. The upper body exoskeleton 108 includes a back link 112 coupled to a hip link 114 and includes an external load support member 116 configured to support an external load 118 and transfer the weight of the external load 118 to the ground through the joints of the lower body exoskeleton 104. It should be understood that any load applied to and/or supported by any part of the exoskeleton may also be considered an external load. The upper body exoskeleton 108 also includes a pair of shoulder straps 120 and a waist strap 121 for securing the upper body exoskeleton 108 to a torso 122 and arms 124 of the human user 102. In this embodiment, the powered exoskeleton 100 does not include articulable arm links, but it should be understood that embodiments of the disclosure would be applicable to arm links or other types of movable links as well.

The lower body exoskeleton 104 includes a pair of upper leg links 126 coupled between the hip link 114 and respective lower leg links 128. Each lower leg link 128 is coupled to a support surface contact member 130 configured to transfer the weight from the external load 118 to a support surface, i.e., to the ground. As used herein, the term "external load" refers to a load that is supported by the powered exoskeleton 100 apart from the structure of the powered exoskeleton 100 and from the human user 102 of the powered exoskeleton 100. Each upper leg link 126 is rotatably coupled to the hip link 114 via an exoskeleton hip joint 132 having an exoskeleton hip joint actuator 134. The exoskeleton hip joint actuator 134 is configured to move, i.e., rotate, the hip link 114 and each upper leg link 126 with respect to each other. Each upper leg link 126 is also rotatably coupled to a respective lower leg link 128 via an exoskeleton knee joint 136 having an exoskeleton knee joint actuator 138 for rotating the upper leg link 126 and the lower leg link 128 with respect to each other. Each lower leg link 128 is rotatably coupled to a respective support surface contact member 130 via an exoskeleton ankle joint 140 having an exoskeleton ankle joint actuator 142 for rotating the lower leg link 128 and the support surface contact member 130 with respect to each other. The exoskeleton joints 132, 136, 140 and links 114, 126, 128 support and transfer the weight of the external load 118, directly and/or indirectly, to the support surface, i.e., to the ground, through the support surface contact member 130.

Each upper leg link 126 is configured to be secured to an upper leg 144 of the human user 102 via an upper leg strap 146, and each lower leg link 128 is configured to be secured to a lower leg 148 of the human user 102 via a lower leg strap 150. It should be understood that the upper leg straps 146, the lower leg straps 150, and other securing elements may include flexible and/or rigid elements, as is known in the art. Each support surface contact member 130 is similarly configured to be secured to a foot 152 of the human user 102 via a foot strap 154. It should also be understood that the above links rotatably move with respect to each other, other types of inter-link movement are contemplated, such as translational movement, as desired.

The different actuators of the powered exoskeleton 100 are each configured to be actuated based on electrochemical reactions detected in the muscles of the human user 102. In this regard, the exoskeleton hip joint actuator 134 may be associated with a plurality of EMG sensors each disposed proximate a respective muscle associated with rotation of the upper leg 144 and torso 122 with respect to each other. In this example, the EMG sensors are skin electrodes configured to engage a skin surface of the human user 102 proximate the respective muscle, but other types of EMG sensors may also be used, such as a subcutaneous electrode configured to be disposed under the skin or an electrode configured to be inserted directly into the muscle itself.

In this example, the torso 122 of the human user 102 includes an EMG back sensor 156 attached thereto and disposed proximate a back muscle 158 (e.g., erector spinae), an EMG abdominal sensor 160 attached thereto and disposed proximate an abdominal muscle 162 (e.g., transverse abdominus), and an EMG gluteal sensor 164 attached thereto and disposed proximate a gluteal muscle 166 (e.g., gluteus maximus). Each upper leg 144 of the human user 102 includes an EMG femoral biceps sensor 168 disposed proximate a femoral biceps muscle 170 and an EMG quadriceps sensor 172 disposed proximate a quadriceps muscle 174.

As will be described in greater detail with respect to FIG. 2, each of the EMG sensors 156, 160, 164, 168, 172 detect electrochemical reactions in the respective muscles 158, 162, 166, 170, 174, and information received from the EMG sensors 156, 160, 164, 168, 172 is used to actuate the associated exoskeleton hip joint actuator 134 based on the information. It should also be understood that more or fewer EMG sensors may be used to determine a resultant actuation of the exoskeleton hip joint actuator 134. In this example, the exoskeleton hip joint 132 is a hinge having one degree of freedom, which in turn allows the exoskeleton hip joint actuator 134 to be a relatively simple rotational actuator, such as a rotational motor, for example. In this example, it may be desirable to determine actuation of the exoskeleton hip joint actuator 134 based on measurements obtained from fewer EMG sensors, in order to conserve costs and simplify operation of the exoskeleton hip joint actuator 134. However, it may also be desirable to provide for actuation that includes rotation about multiple axes and/or translation, in which case it may be desirable to determine actuation of the exoskeleton hip joint actuator 134 based on measurements obtained from more EMG sensors, in order to more accurately reproduce the appropriate rotation and/or translation of the exoskeleton hip joint 132.

The exoskeleton knee joint actuator 138 may be similarly associated with a plurality of EMG sensors, each disposed proximate a muscle associated with rotation of the upper leg 144 and the lower leg 148 with respect to each other. In this regard, in addition to the EMG femoral biceps sensor 168 and the EMG quadriceps sensor 172 associated with the femoral biceps muscle 170 and the quadriceps muscle 174 of the upper leg 144, each lower leg 148 of the human user 102 includes an EMG calf sensor 176 disposed proximate a calf muscle 178 (e.g., gastrocnemius) and includes an EMG shin sensor 180 disposed proximate a shin muscle 182 (e.g., anterior tibialis). As with the exoskeleton hip joint actuator 134 above, the exoskeleton knee joint actuator 138 may use measurements received from one or more of these EMG sensors 168, 172, 176, 180 and/or additional sensors to actuate the exoskeleton knee joint actuator 138. In a similar manner, the exoskeleton ankle joint actuator 142 may use measurements received from one or more of the EMG calf sensor 176, the EMG shin sensor 180 and/or additional sensors, such as an EMG foot sensor 184 associated with a foot muscle 186 to actuate the exoskeleton ankle joint actuator 142. In this embodiment, each of the EMG sensors 156, 160, 164, 168, 172, 176, 180, 184 is electrically connected to one of the exoskeleton joints 132, 136, 140 via an electrical lead wire 188, for communication with one or more controllers (described in greater detail below with respect to FIG. 2), but it should be understood that other communication methods, such as wireless communication, may be used by the EMG sensors 156, 160, 164, 168, 172, 176, 180, 184 to communicate with the one or more controllers.

By measuring several different muscles associated with different joints, the powered exoskeleton 100 can perform complex movements in tandem with actual movements of the human user 102. Unlike reactive or predictive systems that rely on movements of a user that have already occurred, the measurements received from the EMG sensors 156, 160, 164, 168, 172, 176, 180, 184 can be used to accurately determine movement of an associated joint 190, 192, 194 of the human user 102 before the actual movement occurs. In this manner, the powered exoskeleton 100 can enhance the movement of the human user 102 while minimizing resistance by the powered exoskeleton 100 against the actual movements of the human user 102.

An example of a complex movement is illustrated in FIGS. 1A and 1B, in which the human user 102 moves from a squatting position in FIG. 1A to a standing position in FIG. 1B. Before the muscles of the human user 102 actually contract to begin the process of standing up, the brain of the human user 102 sends neurological signals to cause an electrochemical reaction in each of the muscles required. In this simplified example, the EMG back sensor 156 detects an electrochemical reaction in the back muscle 158 and/or the EMG gluteal sensor 164 detects an electrochemical reaction in the gluteal muscle 166, indicating a rotation of at least one skeletal bone (or other type of body segment) in the upper leg 144 (e.g., femur) attached to the gluteal muscle 166 and configured to be rotated by the gluteal muscle 166 with respect to another skeletal bone (e.g., pelvis) attached to the gluteal muscle 166.

The detected electrochemical reactions are translated into EMG signals by the EMG sensors 156, 160 to cause the exoskeleton hip joint actuator 134 to rotate in proportion to a magnitude of the received EMG signals to extend the lower leg 148 with respect to the torso 122. At the same time, the EMG quadriceps sensor 172 detects an electrochemical reaction in the quadriceps muscle 174, indicating a rotation of the lower leg 148 with respect to the upper leg 144 about a knee joint 192 of the human user 102. The detected electrochemical reactions are translated into EMG signals by the EMG quadriceps sensor 172, which are then processed into instructions to cause the exoskeleton knee joint actuator 138 to rotate in proportion to a magnitude of the received EMG signal to extend the lower leg 148 with respect to the upper leg 144. Similarly, the EMG calf sensor 176 detects an electrochemical reaction in the calf muscle 178, indicating an extension of the foot 152 with respect to the lower leg 148 about an ankle joint 194 of the human user 102. The detected electrochemical reactions are translated into EMG signals by the EMG calf sensor 176, to cause the exoskeleton ankle joint actuator 142 to rotate in proportion to a magnitude of the received EMG signal to extend the foot 152 with respect to the lower leg 148.

Different muscle groups may be used by the human user 102 to reverse the process, i.e., move from the standing position to the squatting position. In this example, however, the actuators are configured to actuate based on EMG signals provided by the appropriate EMG sensors for both flexing and extending the respective joints, thereby permitting movement back and forth for the respective joints.

In this embodiment, the powered exoskeleton 100 is driven directly by the actuators 134, 138, 142, but it should be understood that other types of load-bearing exoskeletons may be used. For example, a human user wearing a passive load-bearing exoskeleton (not shown) may use EMG-controlled actuators to cause the human user's body segments to move, which in turn causes the load-bearing links of the passive load-bearing exoskeleton to move, thereby indirectly moving the links of the passive load-bearing exoskeleton using EMG-controlled actuators.

Figure 2:
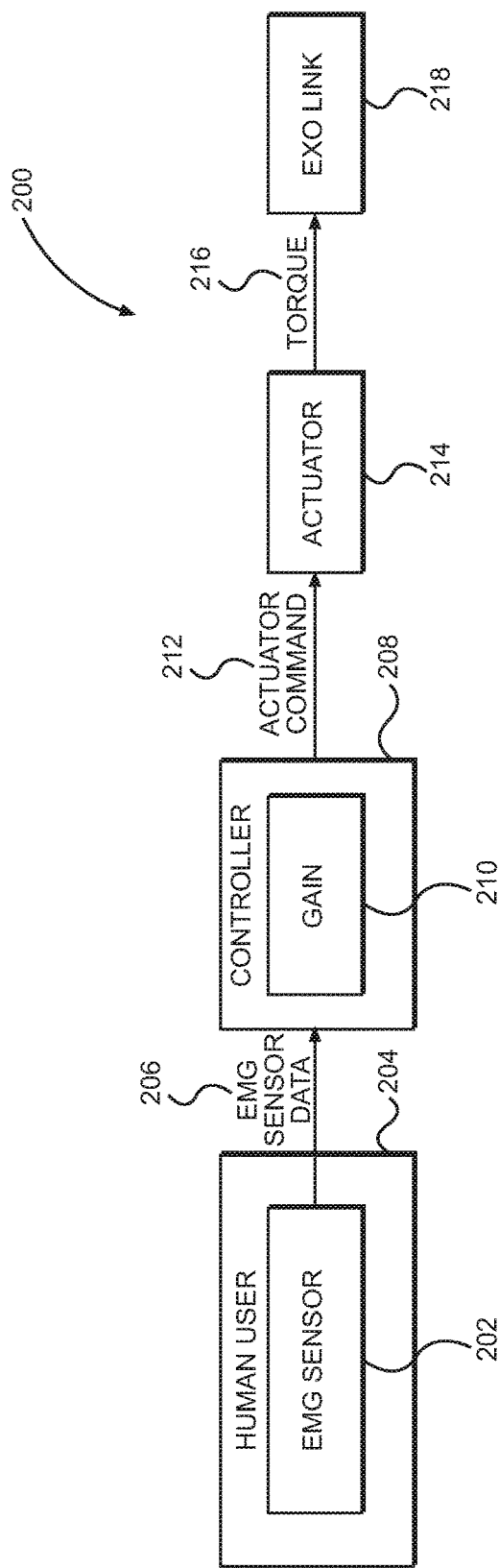
FIG. 2 is a block diagram of a system for exoskeleton control using EMG for direct force amplification, according to an embodiment.

Referring now to FIG. 2, a block diagram of an exoskeleton control system 200 for a powered exoskeleton, such as the powered exoskeleton 100 of FIGS. 1A and 1B, is illustrated according to an embodiment. The exoskeleton control system 200 includes at least one EMG sensor 202 that engages a human user 204 proximate a muscle of the human user 204. Examples of an EMG sensor 202 include the EMG sensors 156, 160, 164, 168, 172, 176, 180, 184 described above with respect to the powered exoskeleton 100 of FIGS. 1A and 1B. The EMG sensor 202 is configured to quantify a muscle contraction of the muscle of the human user 204. This may be accomplished by detecting a magnitude of an electrochemical reaction that occurs in the muscle in response to a neurological instruction from the brain of the human user 204 to contract the muscle.

The EMG sensor 202 provides EMG sensor data 206 based on the detected electrochemical reaction to a controller 208, which may be a single device in communication with multiple EMG sensors 202 or may be a plurality of devices each associated with a subset of EMG sensors 202, as desired. In one embodiment, the EMG sensor data 206 is raw EMG sensor data, which may first be high-pass filtered with a second-order Butterworth filter with a cutoff frequency of about 50 Hz to remove motion artifacts. The signal may then be full wave rectified and low-pass filtered using a second-order Butterworth filter with a cutoff frequency of about 4 Hz. The resulting signal may be referred to as a linear envelope.

The controller 208 then determines a gain 210 for inclusion in an actuator command 212 to be sent to an actuator 214. In this embodiment, the actuator command 212 is a function of the gain 210 and the EMG sensor data 206. For example, the gain 210 may be a predetermined value, and multiplied by a magnitude component of the EMG sensor data 206 to derive the actuator command 212. Notably, in this embodiment, predictive mechanisms are not utilized to determine the actuator command 212, which reduces lag and more closely mimics the natural movements of the human user 204. Examples of an actuator 214 include the actuators 134, 138, 142 described above with respect to the powered exoskeleton 100 of FIGS. 1A and 1B. In response to the actuator command 212, the actuator 214 applies a torque 216 (or other force) containing the gain 210 as a component to one or more exoskeleton links 218.

Using EMG sensor data 206 and a gain 210 to produce an actuator command 212 in this manner may be referred to as direct force amplification, because the exertion force produced by the muscle is directly translated into an amplified torque 216 by the exoskeleton control system 200 in real time. It takes about 50 ms from the generation of the neurological instruction for the electrochemical reaction to occur in the muscle, and it takes about 150 ms from the electrochemical reaction for the muscle to actually contract. Since 50 ms is enough time for the exoskeleton control system 200 to detect the electrochemical impulse, generate the actuator command 212, and apply the torque 216 to the exoskeleton link 218, the exoskeleton control system 200 is able to apply the torque 216 to the exoskeleton link 218 associated with an exoskeleton joint faster than the muscle of the human user 204 can contract. This allows the exoskeleton link 218 to "respond" to movement by the human user 204 before the movement occurs. This in turn reduces fatigue in the human user 204 because the exoskeleton link 218 is already in motion by the time the muscle of the human user 204 is able to exert force against the exoskeleton link 218.

In contrast, a conventional reactive control system requires the muscle of a human user to exert a force against an exoskeleton link to trigger movement of the exoskeleton link. Even if the exertion is small, this causes increased fatigue to the human user over time. Similarly, a conventional predictive control system uses an algorithm to predict future movement of the human user based on predetermined movements for the human user, such as a walking gait. However, if the human user makes a movement that is not predicted by the control system, the human user will exert force against the powered exoskeleton, which also causes increased fatigue over time. By using EMG force amplification, however, the exoskeleton control system 200 of FIG. 2 can accurately mimic and track the movement of the human user 204 in real time, and potentially before the human user 204 actually moves or exerts any force against an exoskeleton link 218. As a result, the exoskeleton control system 200 can be calibrated to apply more gain 210 to the actuator command 212, by adding a calibration value to the gain 210 or multiplying the gain 210 by a calibration value for example, in response to the EMG sensor data 206 indicating an electrochemical reaction having a smaller magnitude. In this manner, more torque 216 can be applied to the exoskeleton link 218 in response to a smaller exertion by the human user 204, and with less exertion by the human user 204 against the exoskeleton link 218 itself. This in turn can allow the human user 204 to carry heavier loads with less fatigue over time.

It should be understood that while the controller 208 in this example is configured to generate the gain 210 to cause the actuator command 212 to be directly proportional, e.g. linearly proportional, to a magnitude component of the EMG sensor data 206, the gain 210 can be generated using additional criteria as well. For example, the controller 208 may be calibrated to take into account a fatigue level of the human user 204. A fatigue level of the human user 204 can be predicted based on the measured EMG sensor data 206 over time, by a predictive algorithm, or by baseline calibration data obtained from the human user 204 via a calibration application. For example, by measuring the EMG sensor data 206 produced by a maximum voluntary contraction of the human user 204's muscle in a controlled environment, an appropriate amount of the gain 210 may be provided so that the human user 204 is not required to reach the maximum voluntary contraction in order to achieve maximum power for the actuator 214. In this manner, by reducing the amount of effort required to produce maximum torque 216 over time, fatigue can be reduced. The calibration value can be based on this maximum voluntary contraction, or on an estimated present voluntary maximum contraction based on a predetermined maximum voluntary contraction of the muscle of the human user and on an estimated fatigue level of the muscle, for example.

Figure 3:
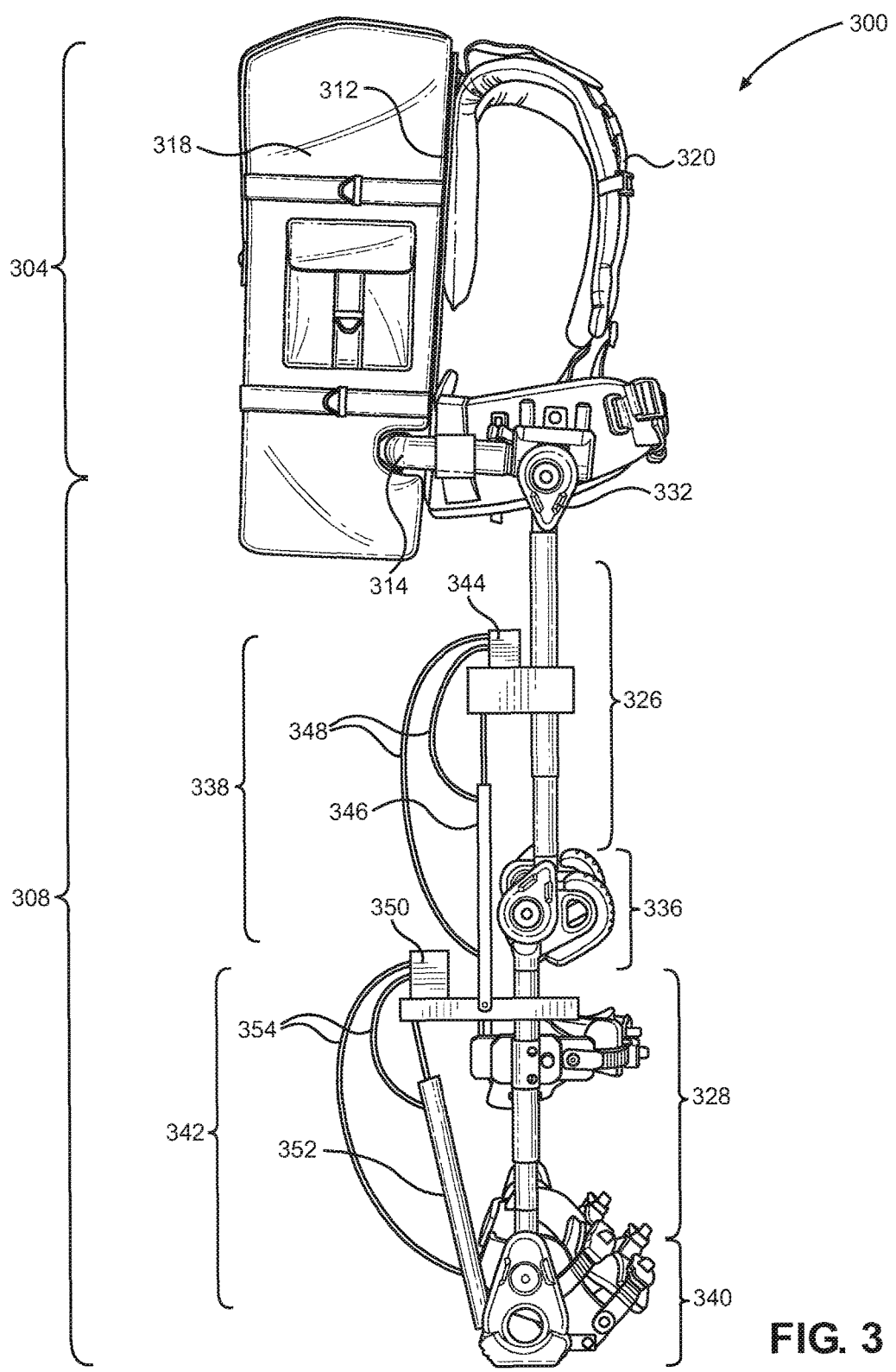
FIG. 3 is a side view of a powered exoskeleton using EMG for direct force amplification, according to another embodiment.

Although the above embodiments use electric motors as the actuators 214, the embodiments are not so limited. In this regard, FIG. 3 is a side view of a powered exoskeleton 300 using EMG for direct force amplification, according to another embodiment. The powered exoskeleton 300 includes an upper body exoskeleton 304, a lower body exoskeleton 308, and many similar components to the powered exoskeleton 100 of FIGS. 1A and 1B, including a back member 312, hip link 314, external load 318 (which is a backpack in this example), shoulder straps 320, upper leg link 326, and lower leg link 328, etc. However, in lieu of the electric exoskeleton knee joint actuator 138 of FIGS. 1A and 1B, an exoskeleton knee joint 336 of FIG. 3 includes an exoskeleton knee joint actuator 338 having a hydraulic pump 344 for powering a hydraulic piston assembly 346. Hydraulic lines 348 are configured to extend and retract the hydraulic piston assembly 346 to flex and extend the exoskeleton knee joint 336 of the powered exoskeleton 300 in response to receiving an actuator command based on received EMG sensor data from EMG sensors disposed proximate to one or more muscles associated with the knee of the human user (not shown). It should be understood that other types of mechanisms, such as a pneumatic pump mechanism, may be used as well.

Similarly, an exoskeleton ankle joint 340 of the powered exoskeleton 300 includes an exoskeleton ankle joint actuator 342 having a hydraulic pump 350 for powering a hydraulic piston assembly 352. Hydraulic lines 354 are configured to extend and retract the hydraulic piston assembly 352 to flex and extend the exoskeleton ankle joint 340 of the powered exoskeleton 300 in response to receiving an actuator command based on received EMG sensor data from EMG sensors disposed proximate to one or more muscles associated with the ankle of the human user (not shown).

Figure 4:
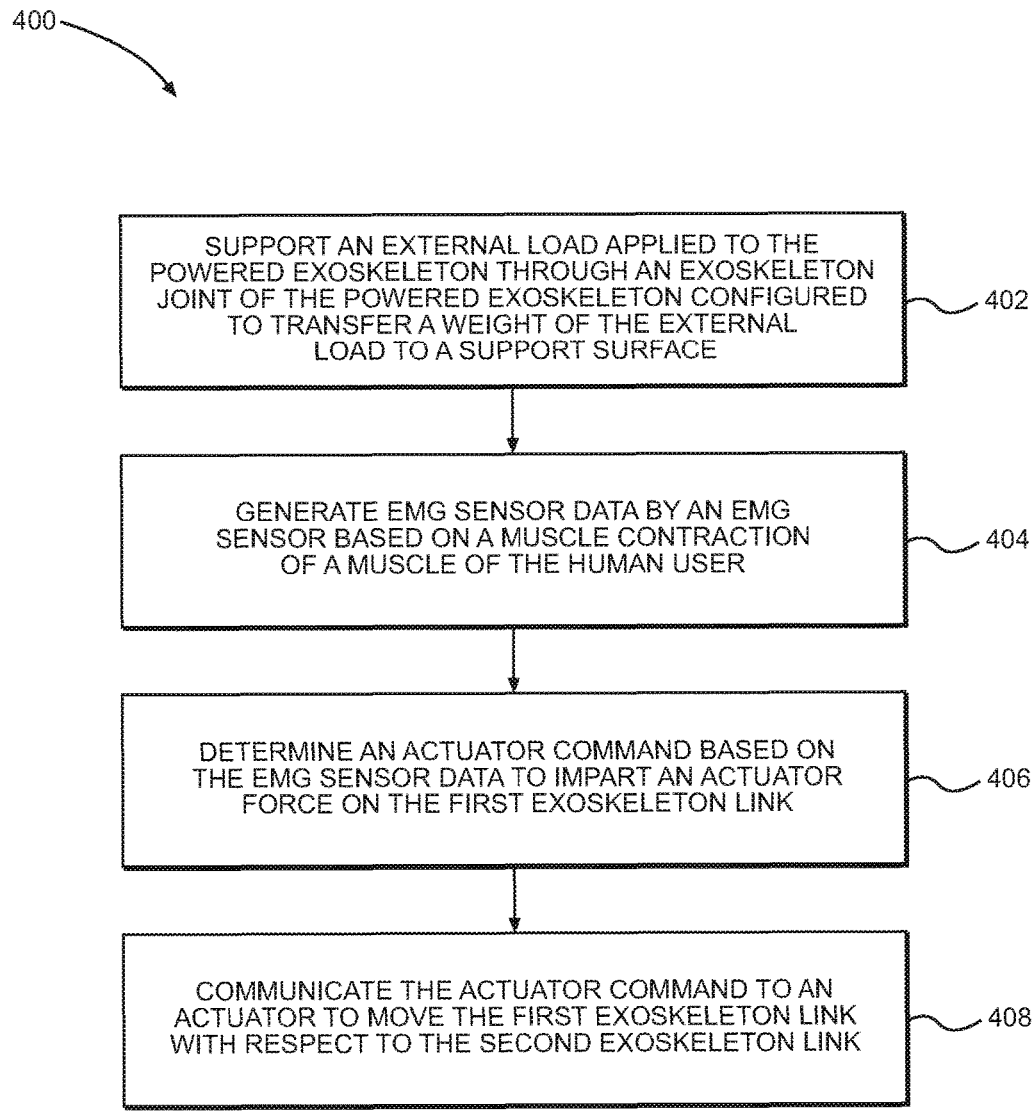
FIG. 4 is a flowchart of a method of operating a powered exoskeleton and a system for exoskeleton control, such as the powered exoskeleton of FIGS. 1A and 1B, and the system of FIG. 2, for example.

FIG. 4 is a flowchart of a method 400 of moving an external load using a powered exoskeleton worn by a human user, such as the powered exoskeleton 100 of FIGS. 1A and 1B, according to an embodiment. The method 400 comprises supporting an external load applied to the powered exoskeleton through an exoskeleton joint of the powered exoskeleton configured to transfer a weight of the external load to a support surface (FIG. 4, block 402). The method 400 further comprises generating EMG sensor data by an EMG sensor based on a muscle contraction of a muscle of the human user (FIG. 4, block 404), and determining an actuator command based on the EMG sensor data to impart an actuator force on the first exoskeleton link (FIG. 4, block 406). The method 400 further comprises communicating the actuator command to an actuator to move the first exoskeleton link with respect to the second exoskeleton link (FIG. 4, block 408).

FIG. 5 is a block diagram of a computing device 500, which may comprise or compose the controller 208 of FIG. 2, according to an embodiment. The computing device 500 includes a processing device 502, a memory 504, and a system bus 506. The system bus 506 provides an interface for system components including, but not limited to, the memory 504, the processing device 502, one or more EMG sensors 202, etc. The processing device 502 can be any commercially available or proprietary processing device or processing devices.

The system bus 506 may be any of several types of bus structures that may further interconnect to a memory bus (with or without a memory controller), a peripheral bus, and/or a local bus using any of a variety of commercially available bus architectures. The memory 504 may include a volatile memory 508 (e.g., random access memory (RAM)) and/or a non-volatile memory 510 (e.g., read only memory (ROM), erasable programmable read only memory (EPROM), electrically erasable programmable read only memory (EEPROM), etc.). A basic input/output system (BIOS) 512 may be stored in the non-volatile memory 510, and can include the basic routines that help to transfer information between elements within the computing device 500. The volatile memory 508 may also include a high-speed RAM, such as static RAM for caching data.

The computing device 500 may further include or be coupled to a computer-readable storage 514, which may comprise, for example, an internal or external hard disk drive (HDD) (e.g., enhanced integrated drive electronics (EIDE) or serial advanced technology attachment (SATA)), HDD (e.g., EIDE or SATA) for storage, flash memory, or the like. The computer-readable storage 514 and other drives, associated with computer-readable media and computer-usable media, may provide non-volatile storage of data, data structures, computer-executable instructions, and the like. Although the description of computer-readable media above refers to an HDD, it should be appreciated by those skilled in the art that other types of media which are readable by a computer, such as floppy disks, magnetic cassettes, flash memory cards, cartridges, and the like, may also be used in the exemplary operating environment, and further, that any such media may contain computer-executable instructions for performing novel methods of the disclosed architecture.

A number of modules can be stored in the computer-readable storage 514 and in the volatile memory 508, including an operating system 516 and one or more program modules 518, which may implement the functionality described herein in whole or in part. It is to be appreciated that the embodiments can be implemented with various commercially available operating systems 516 or combinations of operating systems 516.

A portion of the embodiments may be implemented as a computer program product stored on a transitory or non-transitory computer-usable or computer-readable storage medium, such as the computer-readable storage 514, which includes complex programming instructions, such as complex computer-readable program code, configured to cause the processing device 502 to carry out the steps described herein. Thus, the computer-readable program code can comprise software instructions for implementing the functionality of the embodiments described herein when executed on the processing device 502. As noted above, the processing device 502, in conjunction with the program modules 518 in the volatile memory 508, may serve as the controller 208 for the exoskeleton control system 200 that is configured to, or adapted to, implement the functionality described herein. The computing device 500 may also include a communication interface 520, suitable for communicating with a network as appropriate or desired.

Those skilled in the art will recognize improvements and modifications to the preferred embodiments of the disclosure. All such improvements and modifications are considered within the scope of the concepts disclosed herein and the claims that follow.

What is claimed is:

1. A powered exoskeleton comprising:
a first exoskeleton link configured to support an external load applied to the powered exoskeleton;
a second exoskeleton link movably coupled to the first exoskeleton link at an exoskeleton joint, the second exoskeleton link configured to transfer a weight of the external load through the exoskeleton joint to a support surface;
an actuator configured to selectively move the first exoskeleton link with respect to the second exoskeleton link;
an electromyography (EMG) sensor configured to generate EMG sensor data based on a muscle contraction of a muscle of a human user; and
a controller communicatively coupled to the EMG sensor and the actuator, the controller configured to:
receive the EMG sensor data from the EMG sensor;
determine an actuator command based on the EMG sensor data to impart an actuator force on at least one of the first exoskeleton link and the second exoskeleton link; and
communicate the actuator command to the actuator to cause the actuator to impart the actuator force on the at least one of the first exoskeleton link and the second exoskeleton link to cause the first exoskeleton link and the second exoskeleton link to move with respect to each other.

2. The powered exoskeleton of claim 1, wherein the exoskeleton joint corresponds to a joint of the human user.

3. The powered exoskeleton of claim 2, wherein the first exoskeleton link corresponds to a first body segment of the human user and the second exoskeleton link corresponds to a second body segment of the human user, the muscle attached to at least one of the first body segment and the second body segment and configured to rotate the first body segment and the second body segment with respect to each other about the joint of the human user responsive to the muscle contraction.

4. The powered exoskeleton of claim 1, wherein the EMG sensor comprises an electrode configured to:
engage the human user proximate the muscle;
detect an electrochemical reaction in the muscle corresponding to the muscle contraction of the muscle; and
generate the EMG sensor data in response to detecting the electrochemical reaction in the muscle.

5. The powered exoskeleton of claim 4, wherein the electrode is a skin electrode configured to engage a skin surface of the human user proximate the muscle.

6. The powered exoskeleton of claim 4, wherein the electrode is a subcutaneous electrode configured to be disposed under a skin surface of the human user proximate the muscle.

7. The powered exoskeleton of claim 4, wherein the electrode is further configured to be inserted into the muscle.

8. The powered exoskeleton of claim 7, wherein the actuator command comprises a gain component, wherein the actuator command is directly proportional to a magnitude component of the EMG sensor data by a factor of the gain component.

9. The powered exoskeleton of claim 8, wherein the gain component is at least partially based on a calibration value.

10. The powered exoskeleton of claim 9, wherein the calibration value is based on a predetermined maximum voluntary contraction of the muscle of the human user.

11. The powered exoskeleton of claim 9, wherein the calibration value is based on an estimated present maximum voluntary contraction, wherein the estimated present maximum voluntary contraction is based on a predetermined maximum voluntary contraction of the muscle of the human user and on an estimated fatigue level of the muscle of the human user.

12. A method of moving an external load using a powered exoskeleton worn by a human user, the method comprising:
supporting an external load applied to the powered exoskeleton through an exoskeleton joint of the powered exoskeleton, the exoskeleton joint comprising a first exoskeleton link movably coupled to a second exoskeleton link, the exoskeleton joint configured to transfer a weight of the external load to a support surface;
generating electromyography (EMG) sensor data by an EMG sensor based on a muscle contraction of a muscle of the human user;
determining an actuator command based on the EMG sensor data to impart an actuator force on the first exoskeleton link; and
communicating the actuator command to an actuator coupled to the first exoskeleton link to cause the actuator to impart the actuator force on the first exoskeleton link to move the first exoskeleton link with respect to the second exoskeleton link.

13. The method of claim 12, wherein the exoskeleton joint corresponds to a joint of the human user.

14. The method of claim 13, wherein the first exoskeleton link corresponds to a first body segment of the human user and the second exoskeleton link corresponds to a second body segment of the human user, the muscle attached to at least one of the first body segment and the second body segment and configured to rotate the first body segment and the second body segment with respect to each other about the joint of the human user responsive to the muscle contraction.

15. The method of claim 12, wherein the EMG sensor comprises an electrode configured to:
engage the human user proximate the muscle;
detect an electrochemical reaction in the muscle corresponding to the muscle contraction of the muscle; and
generate the EMG sensor data in response to detecting the electrochemical reaction in the muscle.

16. The method of claim 15, wherein the actuator force comprises a gain component, wherein the actuator force is directly proportional to a magnitude component of the EMG sensor data by a factor of the gain component.

17. The method of claim 16, wherein the gain component is further based on a calibration value.

18. The method of claim 17, wherein the calibration value is based on a predetermined maximum voluntary contraction of the muscle of the human user.

* * * * *